United States Patent [19]

Farrell

[11] Patent Number: 4,695,431
[45] Date of Patent: Sep. 22, 1987

[54] VOLUMETRIC PUMPING APPARATUS AND METHOD FOR SUPPLYING FLUIDS TO SHEATH STREAM FLOW CELLS

[75] Inventor: Gregory A. Farrell, Teaneck, N.J.

[73] Assignee: Technicon Instruments Corporation, Tarrytown, N.Y.

[21] Appl. No.: 766,671

[22] Filed: Aug. 16, 1985

Related U.S. Application Data

[63] Continuation of Ser. No. 408,390, Aug. 16, 1982, abandoned.

[51] Int. Cl.⁴ .................... G01N 1/14; G01N 21/01
[52] U.S. Cl. .................... 422/81; 417/267; 436/52
[58] Field of Search .................... 417/404, 267, 268; 422/55, 63, 81, 82; 436/50, 52–55; 73/863.01, 863.02, 863.03, 863.83, 864.12, 864.21, 864.22, 864.81; 137/2, 3, 10, 93, 571; 356/246

[56] References Cited

U.S. PATENT DOCUMENTS

| | | | |
|---|---|---|---|
| 3,301,189 | 1/1967 | Kling | 417/568 |
| 3,925,018 | 12/1975 | Saunders | 436/165 |
| 3,989,381 | 11/1976 | Fulwyler | 356/39 |
| 4,087,209 | 5/1978 | Mahig | 417/268 |
| 4,135,825 | 1/1979 | Kertscher | 366/79 |
| 4,315,754 | 2/1982 | Ruzicka et al. | 436/52 |
| 4,394,372 | 7/1983 | Taylor | 424/85 |
| 4,428,669 | 1/1984 | Bessis | 356/39 |

FOREIGN PATENT DOCUMENTS

| | | | |
|---|---|---|---|
| 390502 | 2/1924 | Fed. Rep. of Germany | 417/268 |
| 408499 | 1/1925 | Fed. Rep. of Germany | 417/268 |

OTHER PUBLICATIONS

Automatic Analyzer for Multi-Item Clinical Test, Yoshida et al, Hitachi Review, vol. 26, Apr. 1977, No. 4.

*Primary Examiner*—Barry S. Richman
*Assistant Examiner*—Michael S. Gzybowski
*Attorney, Agent, or Firm*—Jeffrey M. Greenman; James J. Romano, Jr.

[57] ABSTRACT

Apparatus and method are provided for the precisely controlled and coordinated supply of sample and sheath stream fluids to a sheath stream flow cell, and comprise the use of positive displacement differential pumping means which are operable to insure consistent sample and sheath stream fluid diameters, velocity and volume flow conditions within the flow cell, thereby maximizing the accuracy and reproducibility of successive analyses.

22 Claims, 1 Drawing Figure

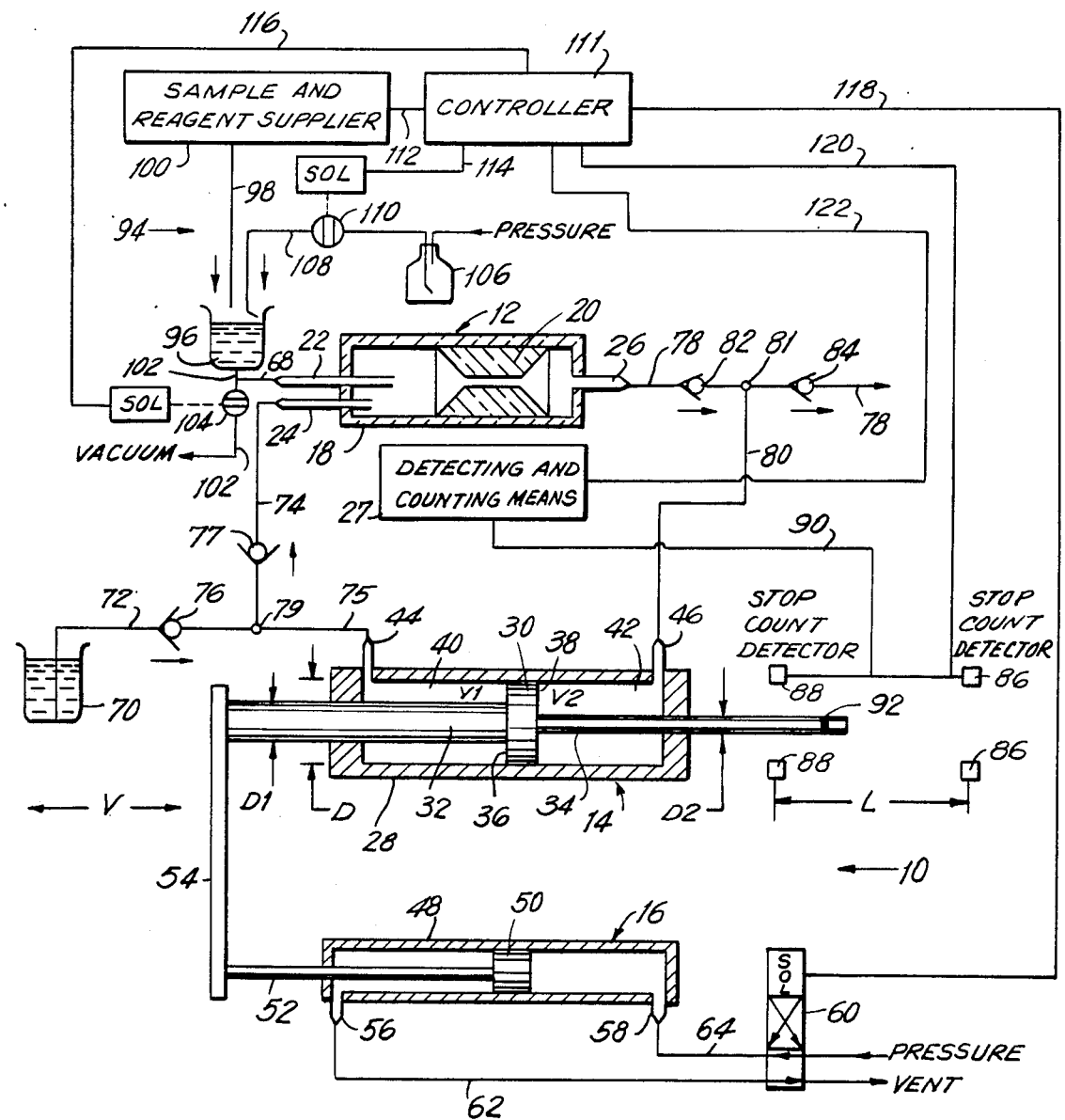

VOLUMETRIC PUMPING APPARATUS AND METHOD FOR SUPPLYING FLUIDS TO SHEATH STREAM FLOW CELLS

This application is a continuation of copending application Ser. No. 06/408,390 filed Aug. 16, 1982 by Mr. Gregory A. Farrell and assigned to the assignee hereof, now abandoned.

BACKGROUND OF THE INVENTION

1. Field of the Invention

This invention relates to volumetric pumping apparatus and method for the precisely controlled and coordinated supply of sheath stream and sample fluids to a sheath stream flow cell for sample analyses; particularly as adapted for high-speed automated biomedical analytical systems.

2. Description of the Prior Art

Although prior art apparatus and methods are known for the supply of sheath stream and sample fluids to sheath stream flow cells, none are known to applicant which can accomplish these functions in the precisely controlled and coordinated manner provided by the teachings of this invention.

In many instances these prior art apparatus and methods utilize peristaltic pumping to supply the sample fluid stream to the flow cell. This is disclosed, for example, in U.S. Pat. No. 3,740,143, wherein peristaltic pumping is used to supply a series of diluted blood samples to a sheath stream flow cell for white blood cell differentiation and counting, and has now been determined in accordance with the teachings of this invention to lead to less than optimal accuracy in cell differentiating and counting due to marginal variations in peristaltic pump roller and pump tube dimensions, which cause variations in the diameter, velocity and/or volume of the sample fluid stream through the flow cell. Since separate pumping systems are used (the sheath stream fluid is pressure pumped from a constantly presurized source in U.S. Pat. No. 3,740,413), variations in the essential sheath-sample fluid streams flow and volume ratios can also occur to further degrade sample analysis accuracy. In addition, peristaltic pumping requires frequent and precise calibration; while the relatively long lengths of peristaltic pump and supply tubing markedly increase the potential for sample carryover. Carryover is defined as the contamination of a succeeding sample by the residue of a preceding sample resulting in loss of accuracy. Further, peristaltic pumping, which operates by the occlusion or squeezing of the pump tubes by the pump rollers, can and does result in damage to the integrity of cells or like sample fluid particles to further degrade accuracy.

Although more current efforts have been made to remedy some of the above-described problems through utilization of separate, finely calibrated peristaltic pumps for each of the sheath stream and sample fluids as described, for example, in paper *HYDRODYNAMICS OF CONCENTRIC PERISTALTIC LAMINAR FLOW OF TWO DIFFERENT FLUIDS* by applicant and I. Beretsky, M.D., presented at the Mar. 23, 1973 meeting of The American Association For Medical Instrumentation at Chicago, Ill., these efforts have not proven fully satisfactory, especially in increasingly sophisticated automated biomedical analytical systems.

Other apparatus and methods are known for the supply of sheath stream and sample fluids to a sheath stream flow cell and, as disclosed in U.S. Pat. No. 3,661,460, use a combination of gravity feed, peristaltic pumping and vacuum pumping, requiring liquid trap, pressure regulation, pressure gauge, and needle valve or other flow restrictor means, to those ends. These apparatus and methods can be difficult to calibrate and tend not to remain calibrated.

In unrelated fields of endeavor, double-acting reciprocating pumps having different effective pumping capacities are exemplified by U.S. Pat. Nos. 2,025,142, 2,163,607, 3,205,825 and 3,713,755 wherein such pumps are disclosed in conjunction with the cooling of gas compressors, the bellows pump-proportioning of high-pressure fluids, the proportioning of fluids for beverage dispensing, and the thrust piston motor means-driven conveyance of fluids, respectively.

Clearly, none of these uses is relevant to the teachings of this invention, which particularly adapt the basic concepts of differential, double acting pumping to the precisely controlled and coordinated supply of sheath stream and sample fluids to a sheath stream flow cell.

OBJECTS OF THE INVENTION

It is, accordingly, an object of the present invention to provide a new and improved apparatus and method for the precisely controlled and coordinated supply of sheath stream and sample fluids to a sheath stream flow cell for sample fluid analyses, thereby maximizing the accuracy of those analyses.

Another object of this invention is the provision of an apparatus and method for the sequential supply of reproducible volumes of each of a series of samples, along with a precisely coordinated volume of a sheath stream fluid, to a sheath stream flow cell under constant sample and sheath stream diameter, velocity and volume flow conditions, in respect of each sample.

Another object of this invention is the provision of an apparatus and method which are particularly adapted for sample particle differentiation and counting, and which are operable with minimal, if any, damage to the sample particles.

Another object of this invention is the provision of an apparatus and method which substantially reduce sample carryover wherein successive samples are supplied, in turn, to the sheath stream flow cell for sequential sample anaylses.

Another object of this invention is the provision of an apparatus and method as above with minimal calibration requirements and maximal calibration retention.

Another object of this invention is the provision of an apparatus and method which are operable at extremely high sample analyses rates.

A further object of this invention is the provision of apparatus and method which can be readily and precisely adjusted, thereby providing versatility of operation.

SUMMARY OF THE INVENTION

A new and improved apparatus and method for the precisely controlled and coordinated supply of sheath stream and sample fluids to a sheath stream flow cell are disclosed, and comprise the use of double acting piston pump means having pumping chambers of different capacities to differentially pump the sheath stream fluid to the flow cell inlet at a first flow rate, and concomitantly aspirate the sheath stream and sample fluids from the flow cell outlet at a second flow rate, thereby establishing the flow rate of the sample fluid through the sheath stream flow cell as the difference between the second flow rate and the first flow rate. The pump piston is driven at constant linear velocity by connected linear actuator drive means to provide for the constancy of all individual fluid flow rates through the flow cell. Detecting means, for detecting a predetermined characteristic of the sample fluid, as the same is flowed through the flow cell, are controlled in phase with the position of the pump piston in the pump cylinder.

The apparatus and method are particularly useful for supplying, in turn, reproducible volumes of each of a series of liquid samples, along with a precisely coordinated volume of a sheath stream liquid to the flow cell with minimal sample carryover, and find application in high-speed, automated biomedical analytical systems.

DESCRIPTION OF THE DRAWINGS

FIG. 1 is a generally schematic diagram of a volumetric pumping apparatus in accordance with the invention depicted in operable relationship with a sheath stream flow cell.

DESCRIPTION OF A PREFERRED EMBODIMENT

Referring now to FIG. 1, volumetric pumping apparatus constructed and operable in accordance with the teachings of this invention are indicated generally at 10, and are depicted in operative relationship with sheath stream flow cell as indicated generally at 12. Apparatus 10 comprises pump means, indicated generally at 14, which operates to supply the sheath and sample fluid streams to the flow cell 12. Pump drive means are indicated generally at 16.

The sheath stream flow cell 12 may, for example, generally take the form of that disclosed in U.S. Pat. No. 3,661,460, cited above, the disclosure of which is hereby incorporated by reference herein. Flow cell 12 comprises a housing 18 and flow chamber 20, with the former including a sample stream inlet 22, sheath stream inlet 24, and a mixed stream outlet 26. Although not, per se, forming part of this invention, it may be understood that the sheath stream flow cell 12 brings the sample and sheath streams introduced at inlets 22 and 24, respectively, together to form a pair of concentric, substantially unmixed streams with the sample stream at the center. Detecting and counting means 27 is operative to count and size particles per unit volume of the sample stream as the ensheathed flows through flow chamber 20. Precise control of the velocity, stability and diameter of the sample stream provides for a precise counting and sizing process.

Pump means 14 comprises a double acting, differential piston pump which includes a pump cylinder 28 having closed ends, and a double acting piston 30 of diameter D reciprocatable therein. Piston rods 32 and 34, of different respective diameters D1 and D2, with D1 being greater than D2, extend from opposed piston faces 36 and 38 through the opposite ends of pump cylinder 28. With piston 30 centrally positioned in pump cylinder 28, pump chambers 40 and 42 have different volumes V1 and V2, respectively, with V1 being smaller than V2. Different pumping capacities are thus provided to opposite sides of piston 30. Such different pumping capacities result from the difference in the effective volumes of chambers 40 and 42 due to the difference in size (volume) of the connecting rods 32 and 34, respectively disposed therein. Equivalent modes of creating this difference in volume are possible.

Sheath fluid inlet/outlet 44 communicates with pump chamber 40, and inlet/outlet 46 communicates with pump chamber 42. Accordingly, first and second, volumetrically different albeit precisely coordinated pumping sections are provided within pump means 14.

As depicted in FIG. 1, the pump drive means 16 comprises a double acting fluid driven linear actuator which includes a drive clyinder 48 having closed ends, and a drive piston 50 reciprocatable therein. A piston rod 52 extends from piston 50 through an end of cylinder 48. A link 54 connects the respective ends of actuator piston rod 52 and pump piston rod 32. Inlet/outlets 56 and 58 are provided at opposite ends of drive cylinder 48. A solenoid operated control valve 60 is operative through conduits 62 and 64, and drive cylinder inlet/outlets 56 and 58, to control the supply of pressurized drive fluid from a non-illustrated source along conduits 62 and 64 alternatively to inlet-outlets 56 and 58 as shown, and simultaneously to alternatively vent such fluid along those conduits from those inlet/outlets, respectively. Accordingly, pump piston 30 is driven by, and in exact unison with, actuator piston 50 at a common velocity V as indicated in FIG. 1. A wide variety of other and different appropriate linear actuators may be utilized.

A sheath stream fluid reservoir 70 is connected to one leg of a three-legged junction 79 by conduit 72. A branch conduit 74 connects junction 79 to flow cell inlet 24; and a branch conduit 75 connects junction 79 to pump inlet/outlet 44. A check valve 76 is disposed along conduit 72 between reservoir 70 and junction 79 to permit fluid flow only from reservoir 70. A check valve 77 is disposed along branch conduit 74 between conduit 72 and flow cell inlet 24 to permit fluid flow only toward inlet 24.

A conduit 78 connects flow cell outlet 26 to waste. Branch conduit 80 connects pump inlet/outlet 46 as shown to three-legged junction 81. Check valves 82 and 84 are disposed along conduit 78 between flow cell outlet 26 and junction 81, and between junctions 81 and the waste disposal end of conduit 78, respectively. Check valve 82 permits fluid flow only from flow cell outlet 26, and check valve 84 prevents fluid inflow to the pump inlet/outlet 46 through conduit 78.

Start and stop count detector means 86 and 88 are operatively connected as shown by connector 90 to the detecting and counting means 27. A mark or like indicia 92 on pump piston rod 34 and is sensed upon its passage between the respective start and stop count detector means 86 and 88 to start and stop, respectively, the operation of detecting means 27. As indicated, start and stop count detector means 86 and 88 are spaced by a distance L.

Sample, reagent and wash liquid supply means are indicated generally at 94, and comprise a reaction chamber 96 to which sample and reagent fluids are supplied through sample and reagent inlet conduit 98 from sample and reagent supplier 100 which may take any known form appropriate for use with automated sample analysis systems. Reaction chamber 96 includes a drain conduit 102 extending downwardly from the chamber bottom to vacuum, and a solenoid operated valve 104 is disposed in drain conduit 102 and is operable to permit or prevent flow therethrough. A reacted sample inlet conduit 68 connects drain conduit 102 above valve 104 to sample inlet 22 of the flow cell.

A constantly pressurized wash liquid reservoir is indicated at 106 and is effective to supply wash liquid to to reaction chamber 96 through wash liquid inlet conduit 108. A solenoid operated valve 110 is disposed in conduit 108 and is operable to permit or prevent flow therethrough.

A controller is indicated schematically at 111 and is operable through connectors 112, 114, 116, 118, 120 and 122 to control and coordinate the respective operations of sample and reagent supplier 100, solenoid controlled valves 110, 104 and 60, start and stop count detectors 86 and 88, and detecting and counting means 27, respectively.

A representative application of the apparatus and method of this invention is the counting and sizing of white blood cells in a series of diluted blood samples as are supplied in turn, with an appropriate reagent quantity, to the reaction chamber 96 by sample and reagent supplier 100 in timed sequence with overall apparatus operation as determined by controller 111. As generally described, an appropriate quantity of at least one sample, and an appropriate quantity of sheath stream fluid are pumped from reaction chamber 96 and reservoir 70 through the flow cell 12 for white cell counting and sizing by movement of pump piston 30 from the right-most to the left-most limits of its stroke in pump cylinder 28 as seen in FIG. 1. The remainder of that sample in reaction chamber 96 is then emptied therefrom, and a wash liquid and the succeeding sample and reagent quantities are supplied thereto in that order. Conversely, movement of pump piston 30 from the left-most to the right-most limits of its stroke in cylinder 28 as seen in FIG. 1 is effective to fill pump 14 with sheath stream fluid from reservoir 70, and pump the previously analyzed sample and sheath stream fluid quantities to waste.

More specifically, with pump piston 30 at the right-most limit of its stroke, pump chamber 40 filled with sheath stream fluid, reaction chamber 96 containing an appropriately reacted quantity of the next sample to be analyzed, and valves 104 and 110 closed as directed by controller 111, it will be clear that actuation of solenoid 60 by controller 111 to reverse pump drive means 16 will operate to commence the drive of pump piston 30 at constant velocity V to the left. Accordingly, the sheath stream fluid in now contracting pump chamber 40 is pumped out at a constant flow rate Q1, through sheath fluid inlet/outlet 44, conduit 75, junction 79, and branch conduit 74 into sheath stream flow cell inlet 24 for flow through the flow cell 12. Concomitantly, the now expanding pump chamber 42 aspirates at a constant combined flow rate Q2 both the sample fluid from reaction chamber 96—through drain 102, conduit 68, flow cell sample fluid inlet 22, the flow cell 12, flow cell outlet 26, conduit 78, junction 81, branch conduit 80 and pump inlet/outlet 46—and the sheath stream fluid from flow cell outlet 26 through conduit 78, junction 81, branch conduit 80 and pump inlet/outlet 46. As flow rates Q1 and Q2 are precisely controlled, the flow rate of the sample fluid passing through the flow cell 12 is likewise precisely controlled. Accordingly, the respective flow rates of the sample and sheath stream fluids through the flow cell 12 are precisely controlled and properly related, with the formation as described hereinabove in the flow cell of the concentric, substantially unmixed sample and sheath streams for analysis of the former.

With incompressible sheath stream and sample fluids, flow rates Q1 and Q2 are precisely defined by the following equations:

$$Q1 = V\pi(D^2 - D1^2)/4 \qquad \text{Equation 1}$$

$$Q2 = V\pi(D^2 - D2^2)/4 \qquad \text{Equation 2}$$

Since, as is shown by FIG. 1, D1 is greater than D2, it must follow that Q2 is greater than Q1, and that the difference therebetween in precisely definable by the following equation:

$$Q2 - Q1 = V\pi/4(D1^2 - D2^2) \qquad \text{Equation 3}$$

In apparatus 10 as illustrated and described, the constant flow rate QSH of the sheath stream fluid from reservoir 70 into and through the flow cell 12 will be precisely equal to Q1, while the flow rate QS of the sample fluid from reservoir 66 into and through the flow cell 12 will also be constant and precisely equal to the difference between Q2 and Q1. Thus will be clear that a precisely controlled differential pumping arrangement is provided for by the utilization as described of double acting pump 28.

The relative dispositions of mark 92 on pump piston rod 34 and the start count detector means 86 are determined such that once a steady state condition of the sheath-sample fluid stream through flow chamber 20 is reached, as described hereinabove, the latter controls detecting and counting means 27 to commence the counting and sizing of the white blood cells in the diluted and reacted blood sample passing through flow chamber 20. The operation of detecting and counting means 27 continues until mark 92, and accordingly the pump piston, have moved the distance L to the left, whereupon stop count detector 88 detects mark 92 and inhibits detecting and counting means 27. Accordingly, cell counting and sizing is effected for a precisely controlled, and readily reproducible, volume of sample fluid.

The detection of mark 27 by stop count detector 88 is also effective, through controller 111, to open valve 104 to rapidly drain the remaining, reacted sample fluid from reaction chamber 96 to vacuum through drain conduit 102. As a result, a segment of air is aspirated from the now empty reaction chamber 96 through drain conduit 102, conduit 68, flow cell inlet 22 and the flow chamber 20 to, in combination with the sheath stream fluid which continues to flow as described through the flow cell 12, commence the removal of the residue of the sample fluid from the flow chamber 20. Shortly thereafter, with piston 30 continuing its driven movement to the left as described, controller 111 is effective to open valve 110 with the result that wash liquid will be pressure pumped from reservoir 106 through conduit 108 to the reaction chamber 96 to wash the residue of the sample fluid therefrom. In addition, some of this wash liquid will be aspirated from the reaction chamber 96 as described to and through the flow cell 12 to remove sample fluid residue from the relevant portion of drain conduit 102, conduit 68 and flow cell inlet 22 and, in combination with the sheath stream fluid which continues to flow through the flow cell, continue sample fluid residue removal from the flow chamber 20.

This removal of sample fluid residue, or washing action, continues—with attendant minimization of sample fluid carryover—until pump piston 30 comes to the left-most limit of its stroke in pump cylinder 28; whereupon controller 111 operates valve 60 to again reverse the direction of movement of drive means 16 to commence the left-to-right stroke of pump piston 30. As this occurs, controller 111 operates to close valves 110 and 104 in that order to assure that all wash liquid is drained from reaction chamber 96, and subsequently directs reagent and sample supplier 100 to supply appropriate quantities of the succeeding sample and reagent to reaction chamber 96.

The left-to-right stroke of pump piston 30 is effective to aspirate sheath stream fluid from reservoir 70 into expanding pump chamber 40 through conduit 72, junction 79, conduit 75 and pump inlet/outlet 44; while concomitantly pumping the commingled sheath stream and reacted sample fluids from contracting pump chamber 42 to waste through pump inlet/outlet 46, conduit 80, junction 81 and conduit 78. As a result, the return of pump piston 30 to the right-most limit of its stroke in pump cylinder 28 will place the apparatus 10 in condition for the next cycle of sample analysis operation as described. This operation continues as described until all of the diluted blood samples in the sample series of interest have been flowed as described through the sheath stream flow cell 12 for cell counting and sizing.

By the above is believed made clear that the particularly significant advantages of the novel apparatus and method include each of the following in full accordance with the heretofore stated objects of this invention:

(a) Precisely the same readily reproducible volume of each of the samples is flowed through sheath stream flow cell 12 attendant each operational cycle of the detecting and counting means 27;

(b) Precisely the same volume of sheath stream fluid is flowed through the sheath stream flow cell 12 attendant each operational cycle of the detecting and counting means 27, thereby precisely coordinating the sample-sheath stream fluid ratio for each of the samples;

(c) The respectively uniform sample and sheath stream volumes of (a) and (b) are flowed through the sheath stream flow cell 12 at precisely the same velocity, thus resulting in precisely the same stable sample fluid stream velocity and diameter, and sample particle velocity, through the flow cell for each of the samples with attendant maximization of compatibility between the operational characteristics of the sheath stream flow cell 12 and the particle detecting and counting means 27;

(d) Damage to the sample fluid particles of interest is minimized (particularly significant with regard to relatively fragile particles such as white or red blood cells) because the same are aspirated rather than positively pumped from sample reservoir 66 to and through sheath stream flow cell 12;

(e) Sample carryover is reduced due to the significantly reduced length of sample fluid conduit 68, the flow cell-purging effects of air segment, wash liquid and sheath fluid flow through flow cell 12 immediately following operation of stop count detector means 88 by mark 92, and the flow cell-purging effect of sample-sheath stream fluid flow through flow cell 12 for each succeeding sample prior to operation of start count detector means 86 by mark 92;

(f) The need for, and complexity of, apparatus calibration is substantially reduced due to the inherently stable operational characteristics of the double acting pump means 14 and the pump drive means 16;

(g) The rate of sample analyses (as limited only by the operational characteristics of the sheath stream flow cell 12 and the particle detecting and counting means 27) is significantly increased due to the excellent high speed operational characteristics of the pump means 14; and (h) Particular ease of precise and consistent adjustment in sample fluid velocity and sample fluid volume through the sheath stream flow cell 12 during operation of the particle counting and detecting means 27 as may respectively be readily accomplished by adjustment in the pressure of the fluid which drives linear actuator means 16, and by adjustment in the distance L between the start and stop count detector means 86 and 88.

All of the above combine to maximize the accuracy, consistency and reproducibility of the sample analysis results, and the reliability and versatility of the apparatus and method of this invention.

Various changes may be made in the disclosed embodiment without departing from the spirit and scope of this invention as defined in the appended claims.

What is claimed is:

1. In an apparatus for establishing a precisely controlled sheath stream flow of first and second fluids from respective sources thereof through a sheath stream flow cell having an inlet and an outlet, the improvements comprising, means for pumping a controlled volume of said first fluid from said (a) source thereof to said flow cell inlet, means integral and cooperating with said first fluid pumping means for aspirating a controlled volume of said second fluid from said (a) source thereof to said flow cell inlet, and means integral and cooperating with said first fluid pumping means and second fluid aspirating means for withdrawing by aspiration at a controlled rate from the outlet of said flow cell a volume of mixed first and second fluids equal to the sum of the volumes the first and second fluids introduced into said flow cell while said first and second fluids are being pumped and aspirated, respectively, into said flow cell inlet by said first fluid pumping means and said second fluid aspirating means.

2. In an apparatus as in claim 1 wherein the improvements further comprise means to detect characteristics of one of said fluids as it is flowed through said sheath stream flow cell, and means operatively associated with said integral fluid pumping and aspirating means and operable to control the operation of said detecting means in response to the operation of said integral fluid pumping and aspirating means.

3. In an apparatus as in claim 1 wherein the improvements further comprise, the means for pumping said first fluid comprises means for pumping a sheath stream liquid and the aspirating means comprises means for aspirating a sample liquid.

4. In an apparatus as in claim 1 wherein the improvements further comprise said first fluid pumping means, second fluid aspirating means and means for withdrawing said mixed first and second fluids comprising an integral differential pump cooperating with respective sources of said first and second fluids and the inlet and outlet of said flow cell.

5. In an apparatus as in claim 1 wherein the improvements further comprise said first fluid pumping means, second fluid aspirating means and means for withdrawing by aspiration said mixed first and second fluids cooperate as means for withdrawing said mixed first and second fluids at a flow rate equivalent to the sum of the flow rates at which said first fluid is pumped and said second fluid is aspirated.

6. In an apparatus as in claim 5 wherein the improvements further comprise, means operatively associated with said first fluid pumping means, second fluid aspirating means and means for withdrawing by aspiration said mixed first and second fluids to drive the same at a substantially constant rate.

7. In an apparatus as in claim 5 wherein the improvements further comprise, the first fluid pumping means is means for pumping a sheath stream liquid, and the second fluid aspirating means comprises means for aspirating a sample liquid for analysis in said sheath stream flow cell.

8. In an apparatus for establishing a precisely controlled sheath stream flow of first and second fluids from respective sources thereof through a sheath stream flow cell having an inlet and an outlet, the improvements comprising, means for pumping a controlled volume of said first fluid from said source thereof to said sheath stream flow cell inlet, means integral and cooperating with said first fluid pumping means for aspirating a controlled volume of said second fluid from said source thereof to said sheath stream flow cell inlet, and means integral and cooperating with said first fluid pumping means and said second fluid aspirating means for withdrawing at a controlled rate from said sheath stream flow cell outlet a volume of mixed first and second fluids equal to the sum of the volumes said first and second fluids introduced into said sheath stream flow cell while said first and second fluids are being pumped and aspirated, respectively, into said sheath stream flow cell inlet by said first fluid pumping means and said second fluid aspirating means; said first fluid pumping means, said second fluid aspirating means, and said means for withdrawing said mixed first and second fluids, respectively comprising an integral differential pump cooperating with said sources of said first and second fluids and the inlet and outlet of said sheath stream flow cell; said differential pump being a double acting piston pump comprising a pump cylinder, a pump piston reciprocatable therein and dividing said pump cylinder into first and second pumping chambers, with the first of said pumping chambers comprising said means to pump the first of said fluids therefrom to said sheath stream flow cell inlet, and the second of said pumping chambers comprising said means to aspirate said second fluid to said sheath stream flow cell inlet and to withdraw the first and second of said fluids through said sheath stream flow cell outlet into said second pumping chamber.

9. In an apparatus as in claim 8 wherein the improvements further comprise, said pump piston comprises opposed piston faces of different effective areas, with the effective area of the piston face for said first pumping chamber being less than the effective area of the piston face for said second pumping chamber, and said second pumping chamber having a greater pumping capacity than the first of said pumping chambers.

10. In an apparatus as in claim 8 wherein the improvements further comprise, said first and second pumping chambers cooperate as means for withdrawing said mixed first and second fluids at a flow rate equivalent to the sum of the flow rates at which said first fluid is pumped and said second fluid is aspirated.

11. In an apparatus as in claim 10 the improvements further comprising, means operatively associated with said differential pump to drive said pump piston at a substantially constant linear velocity.

12. In an apparatus as in claim 11 the improvements further comprising, detecting means operatively associated with said sheath stream flow cell to detect predetermined characteristics of one of said fluids as the same is flowed through said sheath flow cell, and means operatively associated with said pump piston to control the operation of said detecting means in response to the operation of said pump piston.

13. In an apparatus for the positively controlled and coordinated supply of a sheath liquid and a sample liquid from respective sheath liquid and sample liquid sources to sheath stream flow cell analysis means which include a sheath stream flow cell having inlet means and outlet means, the improvements comprising, differential pump means operatively associated with said sheath stream flow cell inlet and outlet means and with the respective sheath liquid and sample liquid sources, said differential pump means being operable to pump said sheath liquid from its source to said sheath stream flow cell inlet means for flow through said sheath stream flow cell, said differential pump means being further operable to concomitantly aspirate said sample liquid from its source through said sheath stream flow cell inlet and outlet means, and said sheath liquid from said sheath stream flow cell outlet means, for concomitant coordinated flow of said sheath and sample liquids through said sheath stream flow cell.

14. In an apparatus as in claim 13 wherein the improvements further comprise, said differential pump means comprise a double acting piston pump which includes a pump cylinder and a pump piston reciprocatable therein and dividing said pump cylinder into first and second, positive displacement pumping chambers, with the first of said pumping chambers being operable to pump said sheath liquid therefrom to said sheath stream flow cell inlet means, and the second of said pumping chambers being operable to concomitantly aspirate said sheath liquid and said sample liquid through said sheath stream flow cell inlet and outlet means into said second pumping chamber.

15. In an apparatus as in claim 13 wherein the improvements further comprise, said sheath liquid source is essentially at ambient pressure.

16. An apparatus as in claim 13 wherein the improvements further comprise, said sample liquid source is essentially at ambient pressure.

17. In an apparatus as in claim 13 wherein the improvements further comprise, a source of a sheath stream flow cell wash liquid, and means connecting said wash liquid source to said sample liquid source for flow of said wash liquid to the latter following the aspiration of said sample liquid from said sample liquid source whereby, said wash liquid may be aspirated from said sample liquid source through said sheath stream flow cell by said differential pump means following the aspiration of said sample liquid therethrough.

18. In an apparatus as in claim 13 wherein the improvements further comprise, said sample liquid source is open to ambient air whereby, ambient air may be aspirated through said sample liquid source and said sheath stream flow cell by said differential pump means following the aspiration of said sample liquid therethrough.

19. In an apparatus as in claim 13 wherein the improvements further comprise, said sheath stream flow cell analysis means further comprise detecting means operatively associated with said sheath stream flow cell and operable to detect predetermined characteristics of said sample liquid as the same is flowed through said sheath stream flow cell, and wherein the improvements further comprise, control means for controlling said detecting means being operatively associated with said differential pump means and operable to control the operation of said detecting means in accordance with the operation of said differential pump means.

20. In an apparatus as in claim 19 improvements further comprise, said differential pump comprises a pump cylinder, a pump piston reciprocatable therewithin, and piston rod means connected to said pump piston and including a piston rod portion which extends without said pump cylinder, said detecting means control means comprising means operatively associated with said piston rod portion and said detecting means and operable to control the operation of said detecting means.

21. In a sheath stream flow cell analysis apparatus for the analysis of sample liquids, the improvements comprising, a source of a sheath liquid, a source of a sample liquid, a sheath stream flow cell having inlet means and outlet means, and a differential pump means operatively associated with said sheath stream flow cell inlet and outlet means and with the respective sources of said sheath liquid and said sample liquid, said differential pump means being operable to pump said sheath liquid from its source to said sheath stream flow cell inlet means for flow through said sheath stream flow cell, said differential pump means being further operable to concomitantly aspirate said sample liquid from its source through said sheath stream flow cell inlet and outlet means, and said sheath liquid from said sheath stream flow cell outlet means, for concomitant coordinated flow of said sheath and sample liquids through said sheath stream flow cell.

22. In an apparatus as in claim 21 wherein the improvements further comprise, said differential pump means comprise a double acting piston pump which includes a pump cylinder and a pump piston reciprocatable therein and dividing said pump cylinder into first and second, positive displacement pumping chambers, with the first of said pumping chambers being operable to pump said sheath liquid therefrom to said sheath stream flow cell inlet means, and the second of said pumping chambers being operable to concomitantly aspirate said sheath liquid and said sample liquid through said sheath stream flow cell inlet and outlet means into said second pumping chamber.

* * * * *